United States Patent [19]

Pines

[11] 3,962,231

[45] June 8, 1976

[54] PREPARATION OF 7-ACYLAMIDO-7-METHOXY-3-SUBSTITUTED METHYL-3(OR 2)-CEPHEM-4-CARBOXYLIC ACID AND ITS S-OXIDES

[75] Inventor: Seemon H. Pines, Murray Hill, N.J.

[73] Assignee: Merck & Co., Inc., Rahway, N.J.

[22] Filed: Oct. 21, 1974

[21] Appl. No.: 516,346

Related U.S. Application Data

[62] Division of Ser. No. 207,980, Dec. 14, 1971, Pat. No. 3,867,378.

[52] U.S. Cl. .............................. 260/243 C; 424/246
[51] Int. Cl.² ...................................... C07D 501/02
[58] Field of Search ................................ 260/243 C

[56] References Cited
UNITED STATES PATENTS 3,853,860   12/1974   Weir .............................. 260/243 C

*Primary Examiner*—Nicholas S. Rizzo
*Attorney, Agent, or Firm*—Walter Patton; J. Jerome Behan

[57] ABSTRACT

A process for preparing 7-acylamido-7-methoxy-3-substituted methyl-3(or 2)-cephem-4-carboxylic acid and its S-oxide and its salts, esters and amides which comprises treating 7-acylamido-7-methoxy-3-methyl-3(or 2)-cephem-4-carboxylic acid and its S-oxide or the salts or ester derivatives thereof with a reagent capable of replacing a hydrogen atom of the 3-methyl radical with a halo, hydroxy or lower alkanoyloxy radical. The products are either antibiotics or are useful intermediates in the preparation of antibiotics.

5 Claims, No Drawings

PREPARATION OF 7-ACYLAMIDO-7-METHOXY-3-SUBSTITUTED METHYL-3(OR 2)-CEPHEM-4-CARBOXYLIC ACID AND ITS S-OXIDES

This is a divisional application of the application U.S. Ser. No. 207,980, filed Dec. 14, 1971, which has issued as U.S. Pat. 3,867,378 on Feb. 18, 1975.

This invention is directed to a novel process for preparing 7-acylamido-7-methoxy-3-substituted methyl-3(or 2)-cephem-4-carboxylic acid and its S-oxides (I) and the non-toxic, pharmaceutically acceptable salts, esters and amide derivatives thereof by treating the corresponding 7-acylamido-7-methoxy-3-methyl-3(or 2)-cephem-4-carboxylic acid (II) or its S-oxide with a reagent capable of replacing a hydrogen atom of the 3-methyl radical with a halo, hydroxy or lower alkanoyloxy radical. Some of the 7-acylamido-7-methoxy-3-substituted methyl-3-cephem-4-carboxylic acids and their salts, esters and amide derivatives obtained in this process are useful as antibiotics whereas other compounds prepared by this process provide a convenient starting material for preparing other cephalosporins substituted in the 3-position by various other radicals.

Those cephalosporin compounds having a 7-methoxy substituent exhibit antibacterial properties similar to the known cephalosporin compounds. However, the 7-methoxy substituted compounds exhibit a broader spectrum of activity.

Cephalosporins having a 7-methoxy substituent are effective against gram negative bacteria including *Escherichia coli, Proteus vulgaris, Proteus mirabilis, Proteus morganii, Salmonella schottmuelleri, Klebsiella pneumoniae AD, Klebsiella pneumoniae B*, and *Paracolobactrum arizoniae* and gram positive bacteria including *Staphylococcus aureus, Streptococcus pyogenes* and *Diplococcus pneumoniae*.

The cephalosporins are useful in removing susceptible microorganisms from pharmaceutical, medical and dental equipment and as bactericides in industrial applications, for example, in water based paints and in the white water of paper mills to inhibit the growth of harmful bacteria.

The instant process comprises a novel process for the functionalization of the 3-methyl radical of the recently discovered 7-methoxy cephalosporins. In general, the process is an oxidation, i.e., the process involves a removal of a hydrogen from the methyl radical. Naturally, the particular function which can be inserted at the 3-methyl position depends on the nature of the particular reagent employed.

This novel process comprises treating an ester of a 7-acylamido-7-methoxy-3-methyl-3(or 2)-cephem-4-carboxylic acid or its S-oxide with a reagent capable of replacing a hydrogen on the 3-methyl group selected from: (1) a halogenating agent such as N-bromosuccinimide, N-bromoacetamide, N-chlorosuccinimide or dibromodimethylhydantoin in the presence of a peroxide such as benzoyl peroxide, tert-butyl peroxide, m-chloro perbenzoic acid and the like or 2,2'-azobisisobutyronitrile in a suitable inert solvent, for example, halogenated alkanes such as chloroform, carbon tetrachloride, dichloromethane, tetrachloroethane and the like or aromatic hydrocarbons such as benzene, chlorobenzene and the like at a temperature in the range of from about room temperature to about 120°C.; (2) selenium dioxide in the presence of a lower alkanol such as ethanol, propanol and the like, a lower alkanoic acid such as acetic acid, propionic acid and the like or in an ether solvent such as dioxane and the like or (3) a metal acetate such as manganese (III) acetate, palladium acetate, mercury (II) acetate, thallium (III) acetate, lead tetraacetate and the like in the presence of a metal halide such as potassium bromide, potassium chloride, potassium iodide and the like, employing acetic acid as a solvent at a temperature in the range from about room temperature to about 80°C. The following equation illustrates this process:

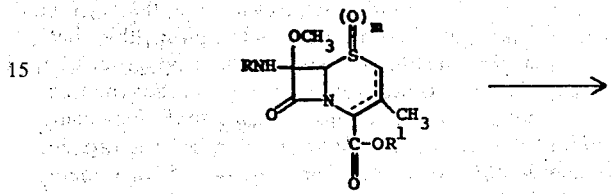

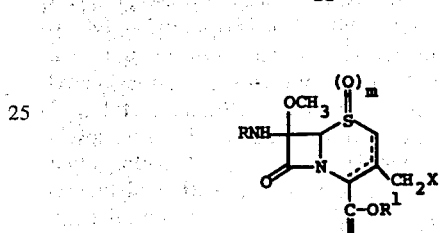

wherein R is an acyl radical, for example, an aliphatic, aromatic, heterocyclic, araliphatic or heterocyclic aliphatic carboxylic acid radical of the formula:

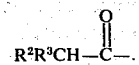

$R^1$ is a blocking group and X is halo such as bromo, chloro and the like, hydroxy or lower alkanoyloxy such as acetoxy, propionyloxy and the like.

The dotted line in formulas I and II indicates that the double bond is in either the $\Delta^2$ or $\Delta^2$ position. When the reagent employed is a halogenating agent the starting compound II is preferably the $\Delta^2$ sulfide or $\Delta^3$ sulfoxide.

The specific reagent which is to be employed in the reaction with the 3-methyl compound naturally depends upon which X group is desired. Also, it should be noted that the choice of solvents influences the nature of the X group which will be obtained.

The following table indicates which reagent and solvent to be employed to obtain the desired X group.

| Reagent | Solvent | X |
| --- | --- | --- |
| 1) Halogenating Agent | Halogenated Alkane or Aromatic hydrocarbons | Halo |
| 2) Selenium Dioxide | Lower alkanol | Hydroxy |
| 3) Selenium Dioxide | Ether type | Hydroxy |
| 3) Selenium Dioxide | Lower alkanoic Acid | Lower alkanoyloxy |
| 4) Heavy Metal Acetate | Acetic Acid | Acetoxy |

Those compounds wherein the acyl radical is of the formula:

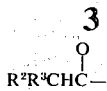

wherein R² and R³ are as defined below, represent a preferred group of radicals because of the generally enhanced antibiotic activity of the Δ³ compounds containing these radicals. R² represents hydrogen, halo, amino, hydroxy, tetrazolyl or carboxy. R³ represents phenyl, substituted phenyl, a 5- or 6-membered monocyclic heterocycle containing one or more oxygen, sulfur or nitrogen hetero atoms in the ring such as furyl, thienyl, thiazolyl, isothiazolyl, oxadiazolyl, thiadiazolyl and the like, substituted heterocycles, phenylthio, heterocyclic or substituted heterocyclic thio groups or cyano. The substituents can be halo, carboxymethyl, aminomethyl, nitro, methoxy or methyl. Especially preferred are those acyl radicals where R² is hydrogen, amino or carboxy and R³ is phenyl or a 5- or 6-membered heterocyclic ring containing from 1 to 2 sulfur, oxygen or nitrogen atoms. Examples of these preferred radicals are phenylacetyl, 3-bromophenylacetyl, p-aminomethylphenylacetyl, 4-carboxymethylphenylacetyl, 2-furylacetyl, 5-nitrofurylacetyl, 3-furylacetyl, 5-chlorothienylacetyl, 5-methoxythienylacetyl, 3-thienylacetyl, 4-methylthienylacetyl, 3-isothiazolylacetyl, 4-methoxyisothiazolylacetyl, 4-isothiazolylacetyl, 3-methylisothiazolylacetyl, 5-isothiazolylacetyl, 3-chloroisothiazolylacetyl, 3-methyl-1,2,5-oxadiazolylacetyl, 1,2,5-thiadiazolyl-4-acetyl, 3-methyl-1,2,5-thiadiazolyl-4-acetyl, 3-chloro-1,2,5-thiadiazolyl-4-acetyl, 3-methoxy-1,2,5-thiadiazolyl-4-acetyl, phenylthioacetyl, 4-pyridylthioacetyl, cyanoacetyl, tetrazolylacetyl, α-fluorophenylacetyl, D-phenylglycyl, 4-hydroxy-D-phenylglycyl, 2-thienylglycyl, 3-thienylglycyl, phenylmalonyl, 3-chlorophenylmalonyl, 2-thienylmalonyl, 3-thienylmalonyl, α-hydroxyphenylacetyl and α-tetrazolylphenylacetyl. An especially preferred substituent is 2-thienylacetyl.

In carrying out this reaction the 4-carboxy group and other carboxy, amino or hydroxy groups in the nucleus are preferably protected with an ester group (R¹ in the formulas), for example, an ester group selected from trichloroethyl, tert-butyl, benzoylmethyl, p-methoxybenzyl, benzyl, benzhydryl, trimethylsilyl, methoxymethyl, benzoylmethylcarbonyloxy, tert-butylcarbonyloxy and the like. These ester groups may be removed by various methods, for example, the benzhydryl or phenylalkyl may be removed by hydrogenation in the presence of a catalyst such as palladium-on-carbon or by treatment with a strong organic or inorganic acid. The tert-butyl or methoxymethyl groups may also be removed by treatment with a strong organic or inorganic acid. Examples of these acids are hydrochloric acid, sulfuric acid, boron trifluoride etherate, formic acid, trifluoroacetic acid, trichloroacetic acid, nitrobenzoic acid and the like.

When the 3-methyl, Δ³ sulfoxides (IIa, infra) are employed they may be reduced to the correspondingly substituted Δ³ sulfides (Ia, infra) by treatment with a reducing agent such as stannous chloride in the presence of a lower alkanoyl halide such as acetyl chloride and the like employing a suitable inert solvent such as acetonitrile, dimethylformamide and the like. The reaction is generally conducted at a temperature in the range of from about 0° up to about 25°C. The following equation illustrates this process:

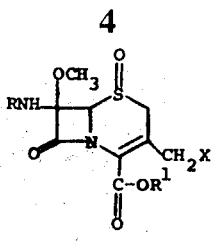

IIa

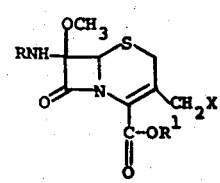

Ia wherein R, R¹ and X are as defined above.

When the Δ² sulfoxides (IIb, infra) are employed they can be converted to the corresponding Δ³-sulfoxide compound (IIa, infra) by treating the Δ²-sulfoxide (IIb) with an isomerizing agent, for example, an alcohol such as methanol and the like or an organic base or an adsorbent such as aluminum, silica gel and the like and then treating the Δ³ sulfoxide (IIa) with a reducing agent, as described above, to obtain the desired 7-acylamido-7-methoxy-3-cephem-4-carboxylic acid ester (Ia). The following equation illustrates this process:

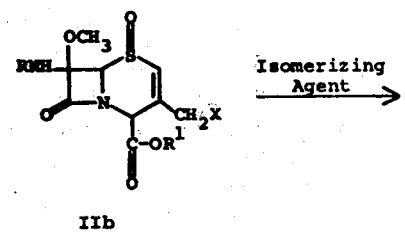

IIb

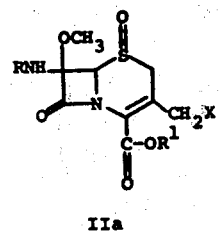

IIa

↓ Reducing Agent

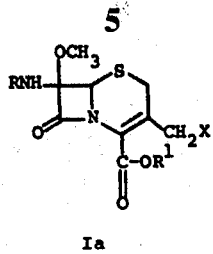

Ia wherein R, R¹ and X are as defined above.

The preparation of the 7-acylamido-7-methoxy-2- (and 3)-cephem-4-carboxylic acids and its corresponding s-oxide and the esters thereof is described in U.S. application Ser. No. 162,703, Theresa Y. Cheng, Sandor Karady, Seemon H. Pines and Meyer Sletzinger filed July 14, 1971.

Included within the scope of this invention are the non-toxic, pharmaceutically acceptable salts of the instant products. In general, any base which will form a salt of the 7-acylamido-7-methoxy-3-substituted methyl-3-cephem-4-carboxylic acid and whose pharmacological properties will not cause an adverse physiological effect when ingested by the body system is considered as being within the scope of this invention. Preferred salts are the sodium and potassium salt derivatives.

Also included in addition to the esters described above are other ester derivatives which are prepared by conventional methods. These include the lower alkyl esters such as methyl ester, ethyl ester and the like.

These non-toxic, pharmaceutically acceptable salts and esters of 7-acylamido-7-methoxy-3-substituted methyl-3-cephem-4-carboxylic acid are the functional equivalent of the corresponding acid.

The following examples illustrate the novel process of this invention. However, the examples are illustrative only and it will be apparent to those skilled in the art that other reagents and solvents similar to those described in the following examples may be employed to afford similar results.

EXAMPLE 1

β,β,β-Trichloroethyl 7-(2-thienylacetamido)-7-methoxy-3-bromomethyl-2-cephem-4-carboxylate A solution of β,β,β-trichloroethyl 7-(2-thienylacetamido)-7-methoxy-3-methyl-2-cephem-4-carboxylate 0.94 g., 2 mmole) in carbon tetrachloride (100 ml.) is heated to reflux. To this refluxing solution is added N-bromosuccinimide (0.4 g., 2.2 mmole) and benzoyl peroxide (0.025 mg.). The reaction mixture is refluxed for 3 more hours, cooled to room temperature and filtered. The filtrate is washed with water and the solvent is removed under vacuum to afford crude product which is dissolved in chloroform and chromatographed on silica gel to afford substantially pure β,β,β-trichloroethyl 7-(2-thienylacetamido)-7-methoxy-3-bromomethyl-2-cephem-4-carboxylate.

EXAMPLE 2

β,β,β-Trichloroethyl 7-(2-thienylacetamido)-7-methoxy-3-bromomethyl-3-cephem-4-carboxy-1-oxide To a refluxing solution of β,β,β-trichloroethyl 7-(2-thienylacetamido)-7-methoxy-3-methyl-3-cephem-4-carboxy-1-oxide (1 g.) in chloroform (100 ml.) is added N-bromosuccinimide (0.5 g.) and tertiary butyl peroxide (0.03 g.). The reaction mixture is refluxed for 3 more hours, cooled to room temperature and filtered. The filtrate is washed with water and the solvent removed to afford β,β,β-trichloroethyl 7-(2-thienylacetamido)-7-methoxy-3-bromomethyl-3-cephem-4-carboxy-1-oxide.

EXAMPLE 3

β,β,β-Trichloroethyl 7-(2-thienylacetamido)-7-methoxy-3-acetoxymethyl-2-cephem-4-carboxylate To a solution of β,β,β-trichloroethyl 7-(2-thienylacetamido)-7-methoxy-3-methyl-2-cephem-4-carboxylate 0.94 (mg., 2 mmole) in acetic acid (10 ml.) is added selenium dioxide (0.111 g., 1 mmole) keeping the reaction temperature at about 25°C. The reaction mixture is stirred for two hours, filtered, diluted with water (30 ml.) and extracted with chloroform. The chloroform extracts are washed successively with water, sodium bicarbonate and water. The solvent is removed under vacuum to afford a residue which is chromatographed on silica gel using chloroform and ethyl acetate (95:5) to afford substantially pure β,β,β-trichloroethyl 7-(2-thienylacetamido)-7-methoxy-3-acetoxymethyl-2-cephem-4-carboxylate.

EXAMPLE 4

β,β,β-Trichloroethyl 7-(2-thienylacetamido)-7-methoxy-3-hydroxymethyl-2-cephem-4-carboxylate To a solution of β,β,β-trichloroethyl 7-(2-thienylacetamido)-7-methoxy-3-methyl-2-cephem-4-carboxylate (0.94 mg., 2 mmole) in ethanol (10 ml.) is added selenium dioxide (0.111 g., 1 mmole) keeping the reaction temperature at about 25°C. The reaction mixture is stirred for two hours, filtered, diluted with water (30 ml.) and extracted with chloroform. The chloroform extracts are washed successively with water, sodium bicarbonate and water. The solvent is removed under vacuum to afford a residue which is chromatographed on silica gel using chloroform and ethyl acetate to afford substantially pure β,β,β-trichloroethyl 7-(2-thienylacetamido)-7-methoxy-3-hydroxymethyl-2-cephem-4-carboxylate.

EXAMPLE 5

Benzhydryl 7-(2-thienylacetamido)-7-methoxy-3-acetoxymethyl-3-cephem-4-carboxylate Manganese (III) acetate (5.0 g.) in acetic acid (60 ml.) is heated to 70°C. under nitrogen. To the stirred solution is added benzhydryl 7-(2-thienylacetamido)-7-methoxy-3-methyl-3-cephem-4-carboxylate (4.0 g.) and potassium bromide (0.5 g.). The solution is maintained at 70°C. for about eight hours. The reaction mixture is cooled and manganese (II) acetate is filtered from the cooled solution. The solvent is removed under vacuum to afford benzhydryl 7-(2-thienylacetamido)-7-methoxy-3-acetoxymethyl-3-cephem-4-carboxylate.

By following substantially the procedure described in Examples 1–5 all of the products of this invention may be prepared. The following equation, together with the following Table I, indicate the starting materials, intermediates and final products which may be prepared by this process:

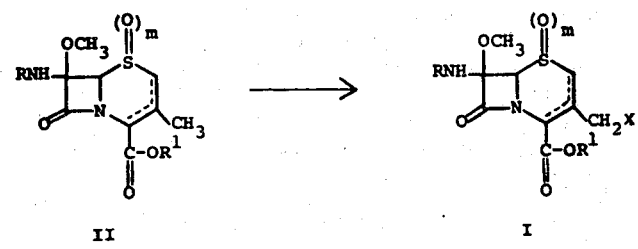

| Example No. | R | R¹ | X | m | Position of Double Bond | Method |
|---|---|---|---|---|---|---|
| 6 | [PhCH(NHC(O)OC(CH₃)₃)C(O)-] | —C(CH₃)₃ | Br | 1 | Δ³ | Ex. 2 |
| 7 | [thienyl-CH₂C(O)-] | —C(CH₃)₃ | Cl | 0 | Δ² | Ex. 1 |
| 8 | [furyl-CH₂C(O)-] | —CH(φ)₂ | —OC(O)CH₃ | 0 | Δ³ | Ex. 3 |
| 9 | [HO-C₆H₄-CH(NHC(O)OCH₂-C₆H₄-OCH₃)C(O)-] | —CH(φ)₂ | —OC(O)CH₃ | 0 | Δ³ | Ex. 3 |
| 10 | [thiazolyl-CH₂C(O)-] | —CH₂C(Cl)₃ | —OH | 0 | Δ³ | Ex. 4 |
| 11 | [phenyl-tetrazolyl-CH-C(O)-] | —CH₂-C₆H₄-OCH₃ | —OC(O)CH₃ | 1 | Δ³ | Ex. 5 |
| 12 | [thienyl-CH₂C(O)-] | —CH(φ)₂ | —OC(O)CH₃ | 1 | Δ² | Ex. 3 |
| 13 | [Ph-CH(C(O)OCH(φ)₂)C(O)-] | —CH(φ)₂ | —OC(O)CH₃ | 1 | Δ³ | Ex. 5 |
| 14 | [thienyl-CH(C(O)OCH(φ)₂)C(O)-] | —C(CH₃)₃ | —OH | 1 | Δ² | Ex. 4 |
| 15 | [Ph-CH₂C(O)-] | —CH₂C(O)-φ | —OH | 0 | Δ³ | Ex. 4 |

-continued

| Example No. | R | R¹ | X | m | Position of Double Bond | Method |
|---|---|---|---|---|---|---|
| 16 | 3-Br-C₆H₄-CH₂-C(O)- | —C(CH₃)₃ | Cl | 0 | Δ² | Ex. 1 |
| 17 | 4-[(CH₃)₃C-O-C(=O)-NH-CH₂]-C₆H₄-CH₂-C(O)- | —CH(φ)₂ | Br | 0 | Δ² | Ex. 1 |
| 18 | 4-[(φ)₂CH-O-C(O)-CH₂]-C₆H₄-CH₂-C(O)- | —CH(φ)₂ | —OCCH₃ (O) | 0 | Δ³ | Ex. 5 |
| 19 | C₆H₅-CH₂-C(O)- | —CH₂-C₆H₄-OCH₃ | —OCCH₃ (O) | 0 | Δ³ | Ex. 5 |
| 20 | 5-NO₂-furan-2-yl-CH₂-C(O)- | —CH₂C(Cl)₃ | —OH | 0 | Δ³ | Ex. 4 |
| 21 | furan-2-yl-CH₂-C(O)- | —CH₂C(O)—φ | —OH | 0 | Δ³ | Ex. 4 |
| 22 | 5-Cl-thien-2-yl-CH₂-C(O)- | —C(CH₃)₃ | Cl | 1 | Δ³ | Ex. 2 |
| 23 | 5-CH₃O-thien-2-yl-CH₂-C(O)- | —CH(φ)₂ | Br | 1 | Δ³ | Ex. 2 |
| 24 | thien-2-yl-CH₂-C(O)- | —CH(φ)₂ | —OH | 0 | Δ³ | Ex. 4 |
| 25 | 5-CH₃-thien-2-yl-CH₂-C(O)- | —CH₂-C₆H₄-OCH₃ | —OH | 0 | Δ³ | Ex. 4 |
| 26 | isothiazol-yl-CH₂-C(O)- | —CH₂C(Cl)₃ | —OCCH₃ (O) | 0 | Δ³ | Ex. 3 |
| 27 | 3-CH₃O-isothiazol-yl-CH₂-C(O)- | —CH₂C(Cl)₃ | —OCC₂H₅ (O) | 0 | Δ³ | Ex. 3 |
| 28 | isothiazol-yl-CH₂-C(O)- | —C(CH₃)₃ | —OCCH₃ (O) | 0 | Δ³ | Ex. 3 |
| 29 | 3-CH₃-isothiazol-yl-CH₂-C(O)- | —CH(φ)₂ | —OCCH₃ (O) | 0 | Δ³ | Ex. 3 |
| 30 | 3-Cl-isothiazol-yl-CH₂-C(O)- | —CH₂-C₆H₄-OCH₃ | —OCCH₃ (O) | 0 | Δ³ | Ex. 3 |

| Example No. | R | R¹ | X | m | Position of Double Bond | Method |
|---|---|---|---|---|---|---|
| 31 | 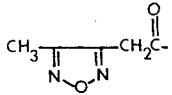 | —CH₂C(O)—φ | —OC(O)CH₃ | 0 | Δ³ | Ex. 3 |
| 32 | 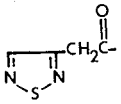 | —CH₂C(O)—φ | —OC(O)CH₃ | 0 | Δ³ | Ex. 3 |
| 33 | 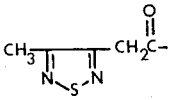 | —CH₁₂C(Cl)₃ | —OC(O)CH₃ | 0 | Δ³ | Ex. 3 |
| 34 | 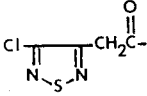 | —CH(φ)₂ | —OC(O)CH₃ | 0 | Δ³ | Ex. 3 |
| 35 | 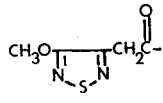 | —CH(φ)₂ | —OC(O)CH₃ | 0 | Δ³ | Ex. 4 |
| 36 | 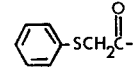 | —C(CH₃)₃ | —OC(O)CH₃ | 0 | Δ³ | Ex. 4 |
| 37 | 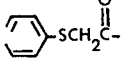 | —C(CH₃)₃ | —OC(O)CH₃ | 0 | Δ³ | Ex. 4 |
| 38 | CNCH₂C(O)— | —CH(φ)₂ | —OC(O)CH₃ | 0 | Δ³ | Ex. 4 |
| 39 | 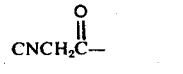 | —CH(φ)₂ | —OC(O)CH₃ | 0 | Δ³ | Ex. 4 |
| 40 | 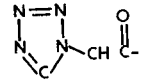 | —CH(φ)₂ | —OC(O)CH₃ | 0 | Δ³ | Ex. 4 |
| 41 | 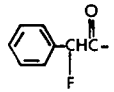 | —CH₂C(O)—φ | —OC(O)CH₃ | 0 | Δ³ | Ex. 4 |
| 42 | 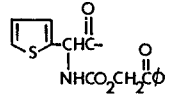 | —CH₂—⌬—OCH₃ | —OC(O)CH₃ | 0 | Δ³ | Ex. 4 |
| 43 | 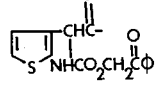 | —C(CH₃)₃ | —OC(O)CH₃ | 0 | Δ³ | Ex. 4 |

-continued

| Example No. | R | R¹ | X | m | Position of Double Bond | Method |
|---|---|---|---|---|---|---|
| 44 | phenyl-CH₂C(O)- | —CH₂C(Cl)₃ | —OC(O)CH₃ | 0 | Δ³ | Ex. 4 |
| 45 | phenyl-CH₂C(O)- | —CH₂CCl₃ | Br | 1 | Δ³ | Ex. 2 |
| 46 | phenyl-CH(OC(O)C(CH₃)₃)C(O)- | —CH(φ)₂ | Cl | 0 | Δ² | Ex. 1 |
| 47 | phenyl-CH₂C(O)- | —CH₂CCl₃ | Br | 0 | Δ² | Ex. 1 |
| 48 | thienyl-CH₂C(O)- | —CH₂OCH₃ | Br | 1 | Δ³ | Ex. 2 |

EXAMPLE A - Reduction of Sulfoxide

Benzhydryl ester of 7-methoxy-3-acetoxymethyl-7-(2-thienylacetamido)-3-cephem-4-carboxylic Acid A solution of benzhydryl ester of 7-methoxy-3-acetoxymethyl-7-(2-thienylacetamido)-3-cephem-4-carboxy-1-oxide (1.3 g.) in acetonitrile (8.0 ml.) and dimethylformamide (5.0 ml.) is stirred at 0°C. To this is added stannous chloride (0.65 g.) and acetyl chloride (0.7 ml.). The reaction mixture is stirred under a nitrogen atmosphere initially at 0°C. for one hour and then at room temperature for an additional hour. Methylene chloride and water are added to the reaction mixture and the organic layer is washed successively with a dilute hydrochloric acid solution, a 5% aqueous sodium bicarbonate solution and sodium chloride saturated solution. After the solvent is removed under vacuum, the residue is chromatographed at 0°C. to yield the benzhydryl ester of 7-methoxy-3-acetoxymethyl-7-(2-thienylacetamido)-3-cephem-4-carboxylic acid.

EXAMPLE B - Isomerization

Benzhydryl ester of 7-methoxy-3-acetoxymethyl-7-(2-thienylacetamido)-3-cephem-4-carboxy-1-Oxide The benzhydryl ester of 7-methoxy-3-acetoxymethyl-7-(2thienylacetamido-2-cephem-4-carboxy-1-oxide is dissolved in methanol (50 ml.) and the solution allowed to stand overnight to afford benzhydryl ester of 7-methoxy-3-acetoxymethyl-7-(2-thienylacetamido)-3-cephem-4-carboxy-1-oxide which is purified by column chromatography (silica gel).

EXAMPLE C - Deblocking

7-Methoxy-3-acetoxymethyl-7-(2-thienylacetamido)-3-cephem-4-carboxylic Acid

A cold solution of the benzhydryl ester of 7-methoxy-3-acetoxymethyl-7-(2-thienylacetamido)-3-cephem-4-carboxylic acid (1.36 gm.) in anisole (10.88 ml.) is stirred with trifluoroacetic acid (5.44 ml.) at 0°C. for one half hour. The volatiles are removed at reduced pressure to afford substantially pure 7-methoxy-3-acetoxymethyl-7-(2-thienylacetamido)-3-cephem-4-carboxylic acid.

We claim:
1. A process for preparing a compound of the formula:

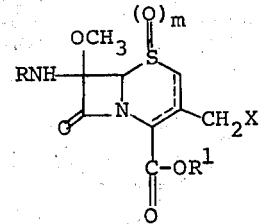

wherein R is an acyl radical of the formula:

wherein
$R^2$ is hydrogen, halo, amino, hydroxy, tetrazolyl or carboxy;
$R^3$ is phenylthio, cyano, phenyl, or substituted phenyl, heterocycle or substituted heterocycle, heterocyclic thio or substituted heterocyclic thio group wherein said heterocycle is selected from the group consisting of furyl, thienyl, thiazolyl, isothiazolyl, oxadiazolyl and thiadiazolyl, and wherein said substituent on the phenyl, heterocycle and heterocyclic thio groups is selected from the group consisting of halo, carboxymethyl, aminomethyl, nitro, methoxy and methyl;
$R^1$ is trichloroethyl, tert-butyl, benzoylmethyl, p-methoxybenzyl, benzyl, benzhydryl, trimethylsilyl, methoxymethyl, benzoylmethylcarbonyloxy, or tert-butyl-carbonyloxy; X is hydroxy or lower alkanoyloxy and *m* is an integer of 0 or 1 which comprises treating a compound of the formula:

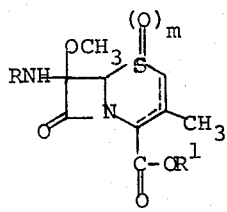

wherein R, R¹ and *m* are as defined above with selenium dioxide in ethanol, propanol, dioxane, acetic acid or propionic acid.

2. A process according to claim 1 for preparing a compound of the formula:

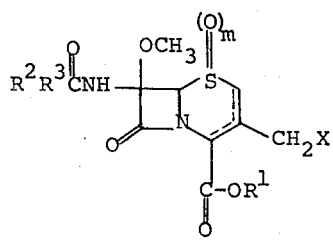

wherein R¹ is trichloroethyl, tert-butyl benzoylmethyl, p-methoxybenzyl, benzyl, benzhydryl, trimethylsilyl or methoxymethyl; R² is hydrogen, amino or carboxy; R³ is phenyl or a 5- or 6-membered heterocyclic ring containing from 1 to 2 sulfur, oxygen or nitrogen atoms wherein said heterocycle is selected from the group consisting of furyl, thienyl, thiazolyl, isothiazolyl, oxadiazolyl and thiadiazolyl; X is hydroxy, acetoxy or propionyloxy and *m* is an integer of 0–1 which comprises treating a compound of the formula:

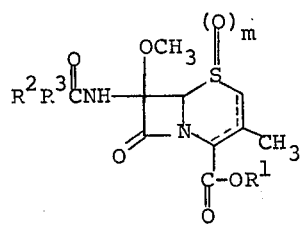

wherein R¹, R², R³ and *m* are as defined above with selenium dioxide in ethanol, propanol, dioxane, acetic acid, or propionic acid in the presence of selenium dioxide.

3. A process according to claim 1 for preparing a compound of the formula:

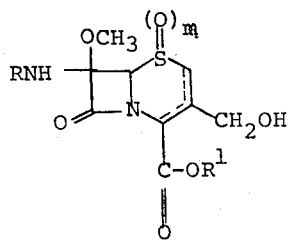

wherein R is an acyl radical of the formula

wherein:
R² is hydrogen, halo, amino, hydroxy, tetrazolyl or carboxy;
R³ is phenylthio, cyano, phenyl or substituted phenyl, heterocycle or substituted heterocycle, heterocyclic thio or substituted heterocyclic thio group wherein said heterocycle is selected from the group consisting of furyl, thienyl, thiazolyl, isothiazolyl, oxadiazolyl and thiadiazolyl, and wherein said substituent on the phenyl, heterocycle and heterocyclic thio groups is selected from the group consisting of halo, carboxymethyl, aminomethyl, nitro, methoxy and methyl;
R¹ is a blocking group selected from the group consisting of: trichloroethyl, tert-butyl, benzoylmethyl, p-methoxybenzyl, benzyl, benzhydryl, trimethylsilyl, methoxymethyl, benzoylmethylcarbonyloxy and tert-butylcarbonyloxy; and *m* is an integer of 0–1 which comprises treating a compound of the formula:

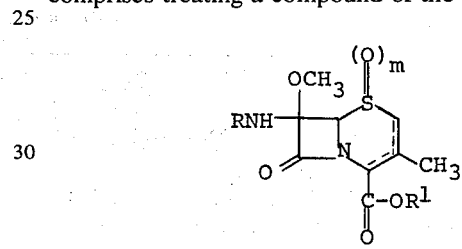

wherein R, R¹ and *m* are as defined above with selenium dioxide in ethanol, propanol or dioxane.

4. A process according to claim 1 for preparing a compound of the formula:

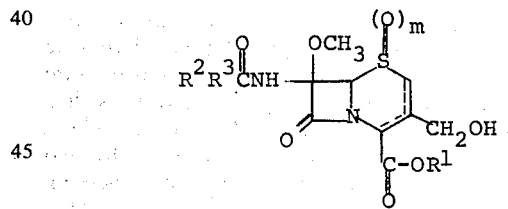

wherein R¹ is trichloroethyl, tert-butyl, benzoylmethyl, p-methoxybenzyl, benzyl, benzhydryl, trimethylsilyl or methoxymethyl; R² is hydrogen, amino or carboxy; R³ is phenyl or a 5- or 6-membered heterocyclic ring containing from 1 to 2 sulfur, oxygen or nitrogen atoms wherein said heterocycle is selected from the group consisting of furyl, thienyl, thiazolyl, isothiazolyl, oxadiazolyl and thiadiazolyl; and *m* is an integer of 0–1 which comprises treating a compound of the formula:

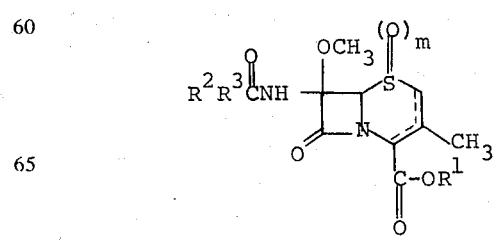

wherein R¹, R², R³ and m are as defined above with selenium dioxide in ethanol, propanol or dioxane.

5. A process according to claim 1 for preparing a compound of the formula:

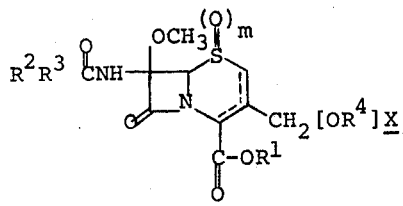

wherein R¹ is trichloroethyl, tert-butyl, benzoylmethyl, p-methoxybenzyl, benzyl, benzhydryl, trimethylsilyl or methoxymethyl; R² is hydrogen, amino or carboxy; R³ is phenyl or a 5- or 6-membered heterocyclic ring containing from 1 to 2 sulfur, oxygen or nitrogen atoms wherein said heterocycle is selected from the group consisting of furyl, thienyl, thiazolyl, isothiazolyl, oxadiazolyl and thiadiazolyl; X is acetoxy or propionyloxy and m is an integer of 0–1 which comprises treating a compound of the formula:

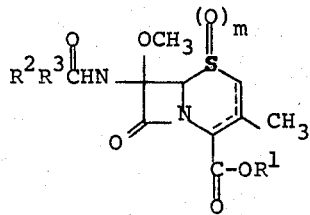

wherein R¹, R², R³ and m are as defined above with selenium dioxide in acetic or propionic acid.

* * * * *

UNITED STATES PATENT OFFICE
CERTIFICATE OF CORRECTION

PATENT NO. : 3,962,231
DATED : June 8, 1976
INVENTOR(S) : Seemon H. Pines

It is certified that error appears in the above-identified patent and that said Letters Patent are hereby corrected as shown below:

Col. 2, line 46 - the second ($\Delta^2$) should read "$\Delta^3$"

Col. 6, line 15 - delete (0.94 (mg., 2 mmole)) and insert "0.94 mg., (2 mmole)"

Col. 11, Example 33 - Col. $R^1$ -
delete ($-CH_2C(Cl)_3$) and insert "$-CH_2C(Cl)_3$"

Col. 11, Example 37 - Col. R -
delete the following structure:

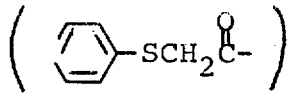

and insert the following structure:

" 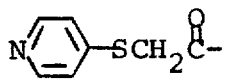 "

Col. 11, Example 39 - Col. R -
delete the following structure:

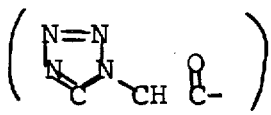

and insert the following structure :

" 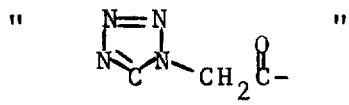 "

UNITED STATES PATENT OFFICE
CERTIFICATE OF CORRECTION

PATENT NO. : 3,962,231
DATED : June 8, 1976
INVENTOR(S) : Seemon H. Pines

It is certified that error appears in the above-identified patent and that said Letters Patent are hereby corrected as shown below:

Col. 13, Line 56, (7-(2thienylacetamido-2-cephem-4-carboxy-1-oxide) should read "7-(2-thienyl-acetamido)-2-cephem-4-carboxy-1-oxide"

Col. 17, Line 5, delete the following in the structure:

( [OR$^4$]$\underline{x}$ )

and insert "X"

Signed and Sealed this

Seventh Day of September 1976

[SEAL]

Attest:

RUTH C. MASON
Attesting Officer

C. MARSHALL DANN
Commissioner of Patents and Trademarks